US008008548B2

(12) United States Patent
De Wit et al.

(10) Patent No.: US 8,008,548 B2
(45) Date of Patent: Aug. 30, 2011

(54) PLANTS WITH REDUCED SUSCEPTIBILITY TO PATHOGENIC OOMYCETES

(75) Inventors: Jacobus Petrus Cornelis De Wit, Oudenbosch (NL); Cornelis Maria Petrus Van Dun, Roosendaal (NL); Johannes Wilhelmus Schut, Wouw (NL); Petrus Lambertus J. Egelmeers, Oud Gastel (NL); Robert Helene Ghislain Dirks, Oudenbosch (NL)

(73) Assignee: Rijk Zwaan Zaadteelt en Zaadhandel, De Lier (NL)

( * ) Notice: Subject to any disclaimer, the term of this patent is extended or adjusted under 35 U.S.C. 154(b) by 842 days.

(21) Appl. No.: 11/628,885

(22) PCT Filed: Jun. 10, 2005

(86) PCT No.: PCT/EP2005/006314

§ 371 (c)(1), (2), (4) Date: Jan. 10, 2008

(87) PCT Pub. No.: WO2005/124108

PCT Pub. Date: Dec. 29, 2005

(65) Prior Publication Data

US 2008/0256661 A1 Oct. 16, 2008

(30) Foreign Application Priority Data

Jun. 16, 2004 (EP) .................................... 04076729

(51) Int. Cl.

| | |
|---|---|
| ***A01H 1/00*** | (2006.01) |
| ***A01H 5/00*** | (2006.01) |
| ***A01H 5/10*** | (2006.01) |
| ***A01H 1/06*** | (2006.01) |
| ***C12N 15/01*** | (2006.01) |
| ***C12N 15/05*** | (2006.01) |

(52) U.S. Cl. ........ 800/301; 800/305; 800/298; 800/295; 800/276

(58) Field of Classification Search ........................ None
See application file for complete search history.

(56) References Cited

FOREIGN PATENT DOCUMENTS

WO WO 02/38727 5/2002

OTHER PUBLICATIONS

Maleck, Klaus et al. "Isolation and Characterization of Broad-Spectrum Disease-Resistant *Arabidopsis* Mutants" Genetics (Apr. 2002) pp. 1661-1671, vol. 160, No. 4.

Dietrich et al. "*Arabidopsis* Mutants Simulating Disease Resistance Response" Cell, Cell Press (May 20, 1994) pp. 565-577, No. 77.

Okubara, Patricia et al. "A Transgenic Mutant of *Lactuca sativa* (lettuce) with a T-DNA Tightly Linked to Loss of Downy Mildew Resistance" Molecular Plant-Microbe Interactions (Nov. 1997) pp. 970-977, vol. 10, No. 8.

Lebeda A. et al. "Host-Parasite Specificity and Defense Variability in the *Lactuca* SPP.—*Bremia lactucae* Pathosystem" Journal of Plant Pathology, Edizioni ETS, Pisa, IT. (2001) pp. 25-35, vol. 83, No. 2.

Maisonneuve B. et al. "Rapid Mapping of Two Genes for Resistance to Downy Mildew from *Lactuca serriola* to Existing Clusters of Resistance Genes" Theoretical and Applied Genetics, Springer, Berlin, DE. (1994) pp. 96-104, vol. 89, No. 1.

Yuen J. et al. "A New Gene for Resistance to *Bremia lactucae*"Phytopathology, St. Paul, MN, US. (1983) pp. 159-162, vol. 73, No. 2.

*Primary Examiner* — Medina A Ibrahim

(74) *Attorney, Agent, or Firm* — Vedder Price P.C.; Thomas J. Kowalski; Deborah L. Lu

(57) ABSTRACT

The present invention relates to a for obtaining a plant showing a reduced susceptibility towards infection with a pathogen, in particular an oomycete, comprising treating MO seeds of a plant species to be modified with a mutagenic agent to obtain M1 seeds and growing plants therefrom the thus obtained M1 seeds to obtain M1 plants, inoculation of the thus obtained M1+n plants with the pathogen and selecting plants that show a reduction or absence of sporulation of the pathogen as plants having a reduced susceptibility phenotype. The invention further relates to plants, seeds, pollen, cells and tissues that have the reduced susceptibility towards oomycetes.

9 Claims, 1 Drawing Sheet

PLANTS WITH REDUCED SUSCEPTIBILITY TO PATHOGENIC OOMYCETES

FIELD OF THE INVENTION

The invention relates to plants, in particular lettuce and spinach plants, which are altered with respect to their mode of interaction with pathogens. More in particular, this invention relates to lettuce (*Lactuca sativa* L.) and spinach (*Spinacia oleracea* L.) that show a modified interaction with oomycetes, in particular downy mildews such as *Bremia lactucae* and *Peronospora farinosa*, that leads to a reduced susceptibility of these crop plant species towards these pathogens.

The invention further relates to methods for obtaining lettuce and spinach plants with altered genotypes, which plants show a reduced susceptibility towards pathogens, in particular the oomycetes *Bremia lactucae* and *Peronospora farinosa*, respectively.

BACKGROUND OF THE INVENTION

Breeding of leafy vegetables like lettuce and spinach aims at the production of commercial varieties optimally adapted to local growing conditions which allows the grower to maximise the productivity of high quality produce. Many characteristics need to be taken into account during selection which relate to both input as well as output traits. One of the most important input traits in this respect relates to disease resistance, in particular to resistance towards oomycetes and more in particular towards downy mildews.

The outcome of the interaction of a plant with a pathogen depends on many genetic factors both of the pathogen as well as the plant. In order to infect a plant successfully, a pathogen needs to overcome a number of barriers.

The first layer is of a physical nature and can be manifested in the form of an enforced cell wall or cuticle layer.

As a second layer of defense, a plant can exhibit a basal form of resistance which may prevent the pathogen from infecting the plant. Non-host resistance can be considered as an extremely successful form of basal defense which in fact is effective for most plant pathogen interactions.

In case the first two barriers have been overcome by the pathogen, a third layer of intricate defense may be encountered in the form of the induction of factors which actively inhibit the infection process initiated by the pathogen. In many different plant pathogen interaction systems such as the interaction of lettuce or spinach with downy mildews, the plant initiates these events only after specific recognition of the invading pathogen. In many cases this recognition occurs after the pathogen has established the first phases of interaction and transferred a so called pathogenicity (or avirulence) factor into the plant cell.

These pathogenicity factors interact with host components in order to establish conditions which are favorable for the pathogen to invade the host and thereby cause disease. When a plant is able to recognize the events triggered by the pathogenicity factors a resistance response can be initiated.

Recognition of these events occurs directly or indirectly by resistance gene (R-gene) products produced by the invaded plant for which recently a mechanistical model, the so-called guard model, has been proposed (Dangl J. L. and Jones, J. D. G. (2001) Nature 411, 826-833). Upon recognition a multicomponent cascade of events takes place including the generation of reactive oxygen species (ROS) leading to a tightly regulated local induction of programmed cell death around the cells which have been infected by the pathogen.

Additionally, genes encoding defense factors such as pathogenesis related or PR proteins are induced which contribute to the execution of the defense response. Also increased callose formation can be induced by recognition of pathogen attack.

Furthermore, the localisation of a pathogen at sites of attempted invasion leads to a systemic induction of the defense response which is called systemic acquired resistance or SAR.

Co-evolution of the plant and the pathogen has led to an arms race in which the resistance can be broken down as a consequence of the capability of the pathogen to interact with and modify alternative host targets or the same targets in a different way. In any case, the recognition is lost and infection can be established successfully resulting in disease. In order to re-establish resistance in a plant, a novel resistance gene has to be introduced which is able to recognize the mode of action of an alternative pathogenicity factor.

Traditionally, plant breeders have been very successful in generating downy mildew resistant lettuce and spinach varieties by making use of resistance genes residing in the wild germ plasm of the crop species.

As the resistance evoked by the R-genes is highly effective, R-genes are exploited at large scale in commercial plant breeding. As a consequence of their mode of action these resistances are not durable as the pathogen population constantly adapts to the newly introduced R-gene. For lettuce, this has resulted in the introduction of over 20 different R-genes in commercial varieties over the last 50 years. As resistance towards downy mildew is a prerequisite for any cultivar to be commercialised, resistance breeding has been given high priority.

As the commercial value of a particular lettuce or spinach variety is primarily determined by its resistance towards the prevailing downy mildew pathotypes in the growing area, the development of novel varieties is largely determined by the ability and velocity of a plant breeder to introgress appropriate downy mildew resistances into the commercial varieties. Furthermore, as the occurrence of novel resistance breaking strains is largely unpredictable, the commercial value of a variety can either last long or diminish rapidly.

Commercial success in lettuce or spinach breeding is therefore largely determined by the availability of effective resistance genes i.e. those genes able to prevent infection by the prevailing downy mildew pathotype, as well as the efficiency of resistance breeding. Thus, a large effort in lettuce and spinach breeding is dedicated towards downy mildew resistance which is primarily beneficial to the crop grower and which may go at the expense of quality traits beneficial to the consumer of fresh produce.

Due to the low durability of the R-gene mediated resistance, a large proportion of the breeding resources in lettuce and spinach has to be allocated towards breeding for downy mildew resistance. It is therefore clear that there exists a need in the art to have available sources of downy mildew resistance in lettuce and spinach which are much more durable as compared to the R-gene mediated resistance. Moreover, it is desirable to have more alleles available that can add to the resistance of a plant against oomycetes.

In the research that led to the present invention, the inventors contemplated that in order to achieve a more durable form of resistance towards downy mildew in lettuce and spinach, other mechanisms than those based on the R-gene mediated recognition and subsequent response should be exploited. As mentioned, several layers of defense exist in a plant which need to be broken down by a pathogen in order to establish disease. More durable forms of resistance may therefore be achieved which act independently of each other and of the specific interaction of an R-gene product and the pathogenicity factor host complex.

For example, it has been shown to be feasible to modify a plant which displays a constitutive form of defense. This means that the defense system is switched on irrespective of inductive signals coming form a successful recognition of a pathogen by a host R-gene product. By modifying factors controlling this response, constitutive activation can be achieved. This can be done through downregulation of repressors or by ectopic activation of inducers of the resistance response. Several methods are available to the person skilled in the art to achieve such downregulation of repressors or ectopic activation of inducers.

In many known cases, however, as a consequence of the constitutive activation of the defense response, resources are reallocated towards defense factors which leads to a significant reduction of plant growth. In commercial crop breeding this yield penalty is obviously not acceptable. Furthermore, part of the defense response can be manifested in the form of the synthesis and accumulation of secondary metabolites which may be lowering the nutritional value of produce or may even be harmful to the health of the consumer.

SUMMARY OF THE INVENTION

It is thus a first object of the invention to generate and identify more durable forms of downy mildew resistance in lettuce and spinach that do not have the above stated drawbacks.

It was then surprisingly found that an alternative approach exists which bypasses the R-gene mediated recognition in lettuce and spinach and which is not manifested as a constitutive form of defense response.

The invention thus relates to a method for obtaining a plant, in particular lettuce or spinach, showing a reduced susceptibility towards infection with a pathogen, in particular an oomycete, comprising:

a) treating M0 seeds of a plant species to be modified with a mutagenic agent to obtain M1 seeds;

b) growing plants from the thus obtained M1 seeds to obtain M1 plants;

c) optionally repeating step b) and c) n times to obtain M1+n seeds and growing plants therefrom;

d) inoculation of the thus obtained M1+n plants with the pathogen;

e) selecting plants that show a reduction or absence of sporulation of the pathogen as plants having a reduced susceptibility phenotype;

f) optionally producing one or more further generations of progeny while selecting for the reduced susceptibility phenotype.

The mutations are suitably induced by means of chemical mutagenesis, which may be performed by contacting the seeds with one or more mutagenic agents, in particular alkylating mutagenic agents, such as ethyl methanesulfonate (ems), diethyl sulfate (des), ethyleneimine (ei), propane sultone, N-methyl-N-nitrosourethane (mnu), N-nitroso-N-methylurea (NMU), N-ethyl-N-nitrosourea (enu), sodium azide.

Alternatively, the mutations are induced by means of irradiation, which is for example selected from x-rays, fast neutrons, UV irradiation.

In another embodiment of the invention the mutations are induced by means of genetic engineering, such as by means of use of chimeric oligonucleotides, homologous recombination, introduction of modified target genes which compete with the endogenous product, downregulation through RNA interference, etc.

The step of selecting plants that show a reduction or absence of sporulation of the pathogen as plants having a reduced susceptibility phenotype is suitably performed by visual inspection.

Preferably the method of the invention further comprises pyramiding of multiple reduced susceptibility alleles.

Production of M1 and M1+n seeds is suitably effected by means of self-pollination.

The invention further provides plants showing a reduced susceptibility towards infection with a pathogen, in particular an oomycete, obtainable by a method as claimed.

Such plant is suitably a lettuce plant (*Lactuca sativa* L.) or a spinach plant (*Spinacia oleracea* L.).

The invention relates to plants, which have in their genome genetic information which is responsible for the reduced susceptibility for oomycetes and is as found in the genome of a lettuce plant as listed in Table 6 of which seed was deposited with the NCIMB on 9 Jun. 2005, which seed has the corresponding accession number as listed in Table 6.

The invention also relates to plants, which have in their genome the genetic information which is responsible for the reduced susceptibility towards oomycetes and is as found in the genome of spinach plants derived from the M2 population RZ03.67551, of which seed is deposited at the NCIMB on 9 Jun. 2005 under accession number . . . .

In a particular embodiment thereof, the invention relates to lettuce plants as listed in Table 6, of which seed was deposited at the NCIMB on 9 Jun. 2005 under the accession numbers given in Table 6.

Another embodiment of the invention is a spinach plant which is derived from the M2 population of seed with the RZ accession number RZ03.67551 as deposited at the NCIMB on 9 Jun. 2005 under NCIMB accession number . . . .

Progeny of the plants as claimed are also part of this invention. "Progeny" as used herein is intended to encompass all plants having the same or a similar reduced susceptibility towards infection with a pathogen, in particular an oomycete, as the original plants described herein and being derived therefrom in any way, such as by crossing, haploid culture, protoplast fusion or other techniques. Such progeny is not only the first but also all further generations as long as the reduced susceptibility is retained.

DETAILED DESCRIPTION OF THE INVENTION

Figure 1:
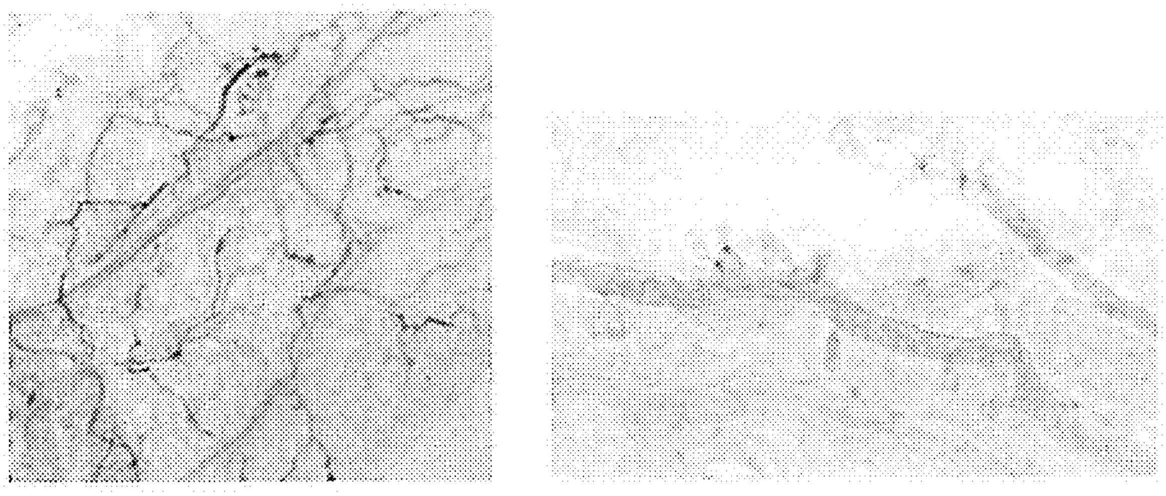
FIG. 1 shows a microscope image of a leaf tissue 6 days after inoculation, showing many clear hyphae and haustoria in a susceptible control variety Baccares.

This form of resistance, which is in fact a reduction in or lack of susceptibility, aims at the modification of host factors required to establish infection by the pathogen. This type of approach was found possible for plant-oomycete interactions especially for lettuce-Bremia as well as spinach-Peronospora interactions, but can also be used for other plant-pathogen combinations.

Identification of the desired modified plants can occur through the establishment of an interaction with an oomycete species for which the starting plant material shows susceptibility. Those mutants which show loss or reduction of susceptibility may contain modified genes which are involved in susceptibility. In practice, identification of a plant containing reduced susceptibility alleles can be done by several means including the inoculation of individual plants of an ems M2 population and visual inspection of the inoculated plants for absence or reduction of sporulation of the pathogen as a consequence of the inability of the pathogen to establish a successful infection. Such screen can be carried out at different levels of plant development including seedlings and adult vegetative or flowering plants.

Moreover further establishment and characterisation of the reduced susceptibility phenotype can be achieved through many sophisticated technologies like fluorescence imaging, transcript profiling and light microscopy. Different phenotypes with respect to these parameters may reflect the generation of different reduced susceptibility genes or different allelic variants of the same reduced susceptibility gene. Allelism tests can simply distinguish between these two possibilities.

Several methods are available to the person skilled in the art to modify genes in a plant species. In a particular embodiment use is made of chemical mutagenesis through treatment with alkylating agents such as ethyl methanesulfonate (ems), diethyl sulfate (des), ethyleneimine (ei), propane sultone, N-methyl-N-nitrosourethane (mnu), N-nitroso-N-methylurea (NMU), N-ethyl-N-nitrosourea (enu), sodium azide.

Additionally, irradiation by x-rays, fast neutrons or UV irradiation can be used to induce gene modification.

Alternatively, genetic engineering technologies for specifically modifying gene targets residing in the genome of a plant can be used. Particularly suitable are chimeric oligonucleotides that are effective mutagens with a specific mode of action. Another approach is to modify gene targets through homologous recombination or gene targeting. Using such approach, a fragment of a gene is exchanged for an introduced DNA fragment containing a desired modification.

The use of genetic engineering technologies in which modified target genes are introduced which compete with the endogenous product is also part of this invention.

Downregulation of specific genes can be achieved through RNA interference.

In case mutagenic oligonucleotides, gene targeting or genetic engineering technologies are used to modify susceptibility factors involved in lettuce-Bremia or spinach-Peronospora interaction, obviously, the primary structure of the gene targets need to be known.

After modification, for example random modification through mutagenesis, of the genes that are involved in the reduction of the pathogen susceptibility, further genetic studies can be carried out in order to map the reduced-susceptibility alleles. In order to achieve this, F2 populations may be generated using the reduced susceptibility mutant and the susceptible wild-type. Phenotyping the resulting F2 plants and genotypic analysis using molecular markers (marker alleles with known genetic map positions) allows to establish the genetic map locations of independently generated reduced susceptibility alleles. Linked marker alleles can be used to select indirectly for the different susceptibility alleles in the offspring.

As a next step, different susceptibility alleles can simply be combined through crossing and selection on the basis of linked molecular markers or distinguishing phenotypic characteristics. This form of so-called gene-pyramiding or gene stacking is also part of this invention.

Moreover, standard map-based cloning techniques allow to identify the gene involved in susceptibility as well as ways to modify these genes such that the host function remains intact whereas the pathogen interaction is abolished.

Identification of susceptibility alleles which reduce the interaction of a plant with a pathogen without affecting host function by direct or indirect means as well as combining these alleles will lead to an even more durable form of downy mildew control in crop systems like lettuce and spinach. In every case, the breeder can decide to stack or pyramid the newly discovered-reduced susceptibility alleles either in combination with each other or with the traditionally known or newly discovered R-genes.

The invention will be further illustrated in the Examples that follow.

EXAMPLES

Example 1

Genetic Modification of Lettuce by Ethyl Methane Sulfonate (ems)

Seeds of the lettuce varieties Troubadour, Apache and Yorvik which are highly susceptible towards *Bremia lactucae* strains Bl:18, Bl:20, Bl:22, Bl:24 and Bl:25 were treated with ems by submergence of approximately 2000 seeds per variety into an aerated solution of either 0.05% (w/v) or 0.07% (w/v) ems during 24 hours at room temperature.

Approximately 1500 treated seeds per variety per ems-dose were germinated and the resulting plants were grown in a greenhouse in the Netherlands from May to September to produce seeds.

After maturation, M2 seeds were harvested and bulked in one pool per variety per treatment. The resulting-6 pools of M2 seeds were used as starting material to identify the individual M2 plants containing reduced susceptibility alleles.

The efficacy of the genetic modification procedure was assessed by determining the occurrence of bleached plants, which is indicative for chlorophyll loss due to modifications in genes directly or indirectly involved in the formation or accumulation of chlorophyll. In all 6 pools of M2 seeds individual plants, which are bleached, were observed which demonstrates that the applied treatments result in genetic modifications.

Example 2

Identification of Lettuce Slants which have Obtained Reduced Susceptibility Alleles The initial identification of M2 plants containing reduced susceptibility alleles as a result of the ems treatment described in Example 1 was carried out by inoculating M2 plants at the seedling level with a suspension of spores of *Bremia lactucae* strains Bl:18 as follows.

Of each of the 6 available M2 pools, approximately 2000 seeds were germinated on wetted filter paper in a closed container to establish an environment of high relative humidity. After seedlings were established i.e. emergence of the cotyledons but the first leaf not yet visible, they were sprayed with the spore suspension of *Bremia lactucae*. The inoculated seedlings were incubated under controlled conditions being 15° C. at 16 hours light, 8 hours dark regime. This seedling test follows more or less the protocol described by Bonnier et al. (New sources of major gene resistance in *Lactuca* to *Bremia lactucae*. Euphytica 61:3, 203-211 (1992)).

After 8 days, infection is clearly established on susceptible control plants derived from the lettuce varieties used for the ems-treatment, which is manifested by the occurrence of sporulating oomycete mycelium at the surface of the cotyledon and which as such can easily be scored. Plants which show a strong reduction or absence of sporulating oomycete biomass are considered to have acquired reduced susceptibility alleles as a consequence of the ems-mediated genetic modification of the starting material.

Table 1 is a summary of the results of the screen for reduced susceptibility towards *Bremia lactucae* strains Bl:18 in different M2 populations of lettuce.

TABLE 1

| treatment | # of seedlings tested (approximately) | *Bremia lactucae* strains tested | # of seedlings showing a strong reduction of or absence of *Bremia lactucae* infection |
|---|---|---|---|
| Troubadour 0.05% ems | 2000 | Bl: 18 | 3 |
| Troubadour 0.07% ems | 2000 | Bl: 18 | 11 |
| Apache 0.05% ems | 2000 | Bl: 18 | 21 |
| Apache 0.07% ems | 2000 | Bl: 18 | 25 |
| Yorvik 0.05% ems | 2000 | Bl: 18 | 7 |
| Yorvik 0.05% ems | 2000 | Bl: 18 | 4 |

As can be observed from Table 1, a total of 71 individual M2 seedlings were identified which show reduced susceptibility towards *Bremia lactucae* strain Bl:18.

In order to confirm the reduced susceptibility, leaf samples were taken of the individual M2 plants at the 10-leaf stage. Two leaf discs per strain were incubated on wetted filter paper in a closed container to establish an environment of high relative humidity and inoculated with spore suspensions of *Bremia lactucae* strains Bl:18 or Bl:22. The inoculated leaf discs were incubated under controlled conditions being 15° C. at 16 hours light, 8 hours dark regime. This leaf disc test follows more or less the protocol described by Bonnier et al. (1992), supra. After 8, 11 and 14 days of incubation, the disease index was scored by manual inspection. The disease index is a measure for the level of infection and discriminates between the categories R (resistance) which means no obvious infection, RS (reduced susceptible) which means a significant reduction of the infection as compared to a susceptible control and S (susceptible) which means heavily infected and strongly sporulating oomycete biomass.

Table 2 summarises the results of this experiment, with more details in Table 3. None of the individuals showed full resistance against both strains, in contrast to standard varieties with resistance based on R-genes. In the case of R-gene mediated resistance it is common practice to assume seedling and leaf disc test as fully interchangeable (see, for example, Bonnier et al., 1992, supra). For known partial resistance against *Bremia* this interchangeability is not the case (Eenink & De Jong, Partial resistance in lettuce to downy mildew (*Bremia lactucae*). 3. Correspondence between resistance levels of cotyledons and leaf discs and resistance of adult plants. Euphytica 31: 761-770 (1982)), but it is surprising to see that they find a good correlation between results from leaf disc tests and observed field resistance and a poor correlation between results from seedling tests and observed field resistance, while in this example the newly found reduced susceptibility shows that the seedling test results are a better prediction for results of field experiment (Example 5) than leaf disc test results.

TABLE 2

Summary of results of leaf disc tests on M2 plants, selected in seedling screen

| | | Bl: 18 | | | | |
|---|---|---|---|---|---|---|
| | | R | NAV | RS | S | Total |
| Bl: 22 | R | 0 | 2 | 1 | 0 | 3 |
| | NAV | 0 | 11 | 0 | 2 | 13 |
| | RS | 3 | 0 | 11 | 8 | 22 |
| | S | 0 | 1 | 7 | 25 | 33 |
| | Total | 3 | 14 | 19 | 35 | 71 |

R = resistant, RS = reduced susceptible; S = susceptible, NAV = not present in the test

Example 3

Phenotypic Characterisation of Progeny of Lettuce Plants Containing Reduced Susceptibility Alleles in Seedling Tests This example describes the identification of M2 plants of lettuce, which have acquired a reduced susceptibility towards *Bremia lactucae*. These M2 plants were grown in the greenhouse to maturity and allowed to set seed by natural self-fertilisation. For each individual selected M2 plant, M3-line seed was harvested. In several cases this M3-seed was sown in a seedling test, as described in Example 2. Less susceptible M3-seedlings were selected from the test and they were grown to mature plants to produce M4-seed by self-fertilisation. The M3- or M4-seeds were subsequently used to confirm the occurrence of reduced susceptibility alleles by testing for reduced susceptibility to *Bremia lactucae* both at the seedling as well as mature plant level. The seedling test is carried out as described in Example 2.

As can be observed in Table 3, using the M3- or M4-lines the reduced susceptibility towards *Bremia lactucae* was confirmed for 32 of the M3- or M4-lines. These results shows that the approach disclosed in this invention allows to generate and identify reduced susceptibility alleles towards *Bremia lactucae* in *Lactuca sativa*.

TABLE 3

Summary of results for 32 confirmed M3- or M4-lines

| mutant nr | original variety | ems-level (%) | M3- or M4-seedling test Bl: 18 (Y, T, A: +) | M3- or M4-field test (standards Y: 4; T: 4; A: 3) | M2-leaf disc test Bl: 18 | M2-leaf disc test Bl: 22 |
|---|---|---|---|---|---|---|
| 1 | Y | 0.05 | (−) | 0 | S | S |

TABLE 3-continued

Summary of results for 32 confirmed M3- or M4-lines

| mutant nr | original variety | ems-level (%) | M3- or M4-seedling test Bl: 18 (Y, T, A: +) | M3- or M4-field test (standards Y: 4; T: 4; A: 3) | M2-leaf disc test Bl: 18 | M2-leaf disc test Bl: 22 |
|---|---|---|---|---|---|---|
| 2 | Y | 0.05 | (−) | 3 | RS | S |
| 3 | Y | 0.05 | (−) | 3 | S | S |
| 4 | T | 0.07 | (−) | 1 | S | S |
| 5 | T | 0.07 | (−) | 1 | RS | RS |
| 6 | T | 0.07 | (−) | 2 | RS | S |
| 7 | T | 0.07 | (−) | 1 | RS | RS |
| 8 | A | 0.05 | (−) | 1 | RS | S |
| 9 | A | 0.05 | (+) | 2 | RS | S |
| 10 | A | 0.05 | (−) | 1 | S | S |
| 11 | A | 0.05 | (−) | 1 | R | RS |
| 12 | A | 0.05 | (−) | 1 | RS | S |
| 15 | A | 0.05 | (−) | 1 | RS | RS |
| 16 | A | 0.05 | (−) | 2 | S | S |
| 17 | A | 0.05 | (−) | 2 | S | S |
| 18 | A | 0.07 | (−) | 2 | S | RS |
| 19 | A | 0.07 | (−) | 1 | RS | RS |
| 20 | A | 0.07 | (−) | 2 | S | RS |
| 22 | A | 0.07 | (−) | 2 | RS | RS |
| 24 | A | 0.07 | (−) | 1 | S | RS |
| 25 | A | 0.07 | (−) | 2 | S | RS |
| 26 | A | 0.05 | (−) | 2 | S | S |
| 27 | A | 0.07 | (−) | 1 | S | RS |
| 28 | Y | 0.05 | (+) | 2 | NAV | NAV |
| 29 | T | 0.05 | (−) | 2 | S | S |
| 42 | A | 0.07 | (+) | 1 | NAV | NAV |
| 44 | A | 0.07 | (−) | 2 | S | NAV |
| 45 | T | 0.07 | − | 1 | RS | RS |
| 46 | A | 0.07 | (−) | 1 | S | S |
| 47 | A | 0.07 | (+) | 1 | S | RS |
| 48 | A | 0.07 | (+) | 1 | S | S |
| 49 | A | 0.07 | (−) | 1 | S | NAV |

Original varieties: A = Apache, T = Troubadour, Y = Yorvik; seedling test: − = no sporulation, (−) = sporulation with a few spores, (+) = light sporulation, + = full sporulation; field test: 0 = resistant, 5 = very susceptible; leaf disc test: see Table 2. Seedling and field test results for the original varieties are included in the table headers. Field test data are based on combined results of 2002 and 2003. Seedling test results are based on M3-lines and, where available, M4-lines. Segregation of reduced susceptibility alleles is not included in this table.

Example 4

Cytological Characterisation of Progeny of Lettuce Slants Containing Reduced Susceptibility Alleles In addition to the test described in Example 3, another seedling test is performed using the fysio Bl:24. The seedling test is carried out as described in Example 2. The original varieties Apache, Troubadour and Yorvik are susceptible for this fysio. Another susceptible variety, Bacares, was used as susceptible standard, and the variety Hillary was used as a resistant standard, based on R-gene mediated response.

Figure 2:
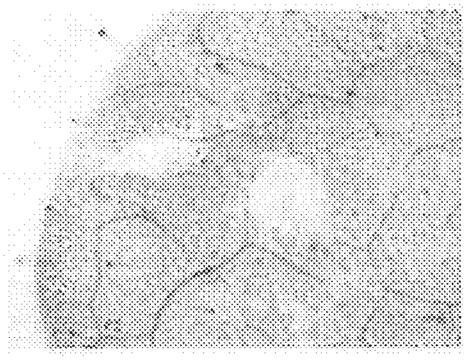
FIG. 2 shows a microscope image of a leaf tissue showing absence of hyphae and haustoria of resistant control variety Hillary.

Six days after inoculation, leaves were sampled and trypan blue staining was performed as described below to be able to observe the growth of the *Bremia* pathogen in the leaf (for standard examples, see FIGS. 1 and 2). The 32 confirmed M3-lines or their reduced susceptible offspring showed no or reduced *Bremia* development in the leaf, in comparison with the susceptible standard. See Table 4.

The reduced susceptibility towards Bl:24 in Example 4, Bl:18 in Example 2 and 3, and Bl:22 in Example 3, shows no fysio-specificity, which is in contrast to strongly fysio-specific R-gene mediated resistance (see for example Bonnier et al., 1992, supra).

Lactophenol Trypan Blue Staining for Downy Mildew in Plants

*Bremia* infected leaves of lettuce are collected and put into microtubes. Lactophenol Trypan Blue (per 100 ml: 25 ml lactic acid, 25 ml glycerol, 25 ml phenol, 25 ml water, 25 mg trypan blue) is added to cover the leaves completely. The mixture is subsequently heated at 100° C. for 5 minutes and then allowed to cool down to room temperature. Trypan blue is removed and the same volume of chloral hydrate (per 100 ml: 80 g chloral hydrate, 30 ml water, 10 g glycerol) is added to destain the leaf sample which is done overnight. The sample is treated in a Speedvac for approximately 5 minutes to remove air bubbles from the leaf samples. Subsequently the leaf samples are spread onto a microscope glass slide for microscopy.

TABLE 4

Summary of microscopic observations of *Bremia* development in leaf tissue 6 days after inoculation with fysio Bl: 24. Mutant number is indicating the original M2-plant with reduced susceptibility, from which the observed plant is descending. This number is comparable with mutant numbers in Table 3.

| mutant nr | hyphae | haustoria | sporulation |
|---|---|---|---|
| 1 | 0 | 0 | 0 |
| 2 | 0 | 0 | 0 |
| 3 | 0 | 0 | 0 |
| 4 | 0 | 0 | 0 |
| 5 | 0 | 0 | 0 |
| 6 | 2 | 1 | 0 |
| 7 | 3 | 3 | 0 |
| 8 | 0 | 0 | 0 |
| 9 | 3 | 2 | 0 |
| 10 | 1 | 1 | 0 |
| 11 | 0 | 0 | 0 |

TABLE 4-continued

Summary of microscopic observations of *Bremia* development in leaf tissue 6 days after inoculation with fysio Bl: 24. Mutant number is indicating the original M2-plant with reduced susceptibility, from which the observed plant is descending. This number is comparable with mutant numbers in Table 3.

| mutant nr | hyphae | haustoria | sporulation |
|---|---|---|---|
| 12 | 0 | 0 | 0 |
| 15 | 0 | 0 | 0 |
| 16 | 0 | 0 | 0 |
| 17 | 0 | 0 | 0 |
| 18 | 2 | 1 | 0 |
| 19 | 0 | 0 | 0 |
| 20 | 1 | 0 | 0 |
| 22 | 0 | 0 | 0 |
| 24 | 0 | 0 | 0 |
| 25 | 0 | 0 | 0 |
| 26 | 0 | 0 | 0 |
| 27 | 0 | 0 | 0 |
| 28 | 2 | 2 | 0 |
| 29 | 0 | 0 | 0 |
| 42 | 2 | 1 | 0 |
| 44 | 1 | 0 | 0 |
| 45 | 0 | 0 | 0 |
| 46 | 0 | 0 | 0 |
| 47 | 1 | 1 | 0 |
| 48 | 2 | 1 | 0 |
| 49 | 0 | 0 | 0 |
| Baccares (suceptible) | 3 | 3 | 3 |

Scoring (hyphae, haustoria, sporulation): 0 = absent, 1 = strongly reduced, 2 = reduced, 3 = similar as susceptible standard (Bacares)

Example 5

Phenotypic Characterisation of Progeny of Lettuce Plants Containing Reduced Susceptibility Alleles in Field Trials Mature lettuce plants were tested in unreplicated field trials in 2002 and 2003 with a strong natural *Bremia*-infection (strain Bl:24 and Bl:25). Both trials were located in Fijnaart, the Netherlands. Seeds were sown in July, young plants planted in August, and mature plants judged in the second half of September and the beginning of October. Each M3-line or its reduced susceptible offspring was represented by a plot of 24 plants. At the mature stage, the final level of disease was scored on a progressive scale of 0-5 in which 0 stands for absence of disease symptoms and 5 stands for heavily diseased. R-gene resistant plants as well as the susceptible original lines were included as controls. The results are shown in Table 3.

Example 6

Genetic Modification of Spinach by Ethyl Methane Sulfonate (ems)

Seeds of the spinach line F5 (755*265)*BLLT which is highly susceptible towards *Peronospora farinosa* races Pfs 5,6 and 7 were treated with ems by submergence of approximately 10.000 seeds into an aerated solution of 0.3% (w/v) ems during 24 hours at room temperature. The treated seeds were germinated and grown in a greenhouse to induce bolting and flowering.

After maturation, M2 seeds were harvested and bulked in one pool. The resulting pool of M2 seeds is used as starting material to identify the individual M2 plants containing reduced susceptibility alleles. This pool is deposited under RZ accession number 03.67551 with the NICMB on 9 Jun. 2005 under NCIMB accession number . . . .

The efficacy of the genetic modification procedure was assessed by determining the occurrence of bleached plants which is indicative for chlorophyll loss due to modifications in genes directly or indirectly involved in the formation or accumulation of chlorophyl. In the pool of M2 seeds individual plants which are bleached were observed which demonstrates that the applied treatments result in genetic modifications.

Example 7

Identification of Spinach Plants which have Obtained Reduced Susceptibility Alleles The initial identification of M2 plants containing reduced susceptibility alleles as a result of the ems treatment described in Example 6 was carried out by inoculating M2 plants at the seedling level with suspensions of spores of *Peronospora farinosa* race Pf7.

Approximately 10.000 seeds of the available M2 pool were germinated on wetted filter paper in a closed container to establish an environment of high relative humidity. After seedlings were established i.e. emergence of the cotyledons but the first leaf not yet visible, they were sprayed with the spore suspension of *Peronospora farinosa*. The inoculated seedlings were incubated under controlled conditions being 14° C. at 14 hours light, 10 hours dark regime.

After approximately 8 days, infection is clearly established on susceptible control plants derived from the spinach line used for the ems-treatment, which is manifested by the occurrence of sporulating oomycete mycelium at the surface of the cotyledon and which as such can easily be scored. Plants which show a strong reduction or absence of sporulating oomycete biomass are considered to have acquired reduced susceptibility alleles as a consequence of the ems-mediated genetic modification of the starting material.

In total, 36 individual M2 seedlings were identified which show reduced susceptibility towards *Peronospora farinosa* race Pfs:7.

Example 8

Phenotypic Characterisation of Progeny of Spinach Plants Containing Reduced Susceptibility Alleles This Example describes the identification of M2 plants of spinach which have acquired a reduced susceptibility towards *Peronospora farinose* race Pfs:7. These M2 plants were grown in the greenhouse to maturity and allowed to set seed. From the 36 individual selected M2 plants, an M3 seed generation was harvested from 32 of them. The M3 seeds are subsequently used to establish the occurrence of reduced susceptibility alleles by testing for reduced susceptibility to *Peronospora farinosa* at the seedling level. The seedling test is carried out as described in Example 7.

In Table 5, the reduced susceptibility towards *Peronospora farinosa* was confirmed in four M3 populations. This results shows that the approach disclosed in this invention allows to generate and identify reduced susceptibility alleles towards *Peronospora farinosa* in spinach.

Deposit Information

Seeds of various lettuce plants and one spinach M2 population (at least 2500 of each) of the invention were deposited on 9 Jun. 2005 under the terms of the Budapest Treaty with the NCIMB in Aberdeen (NCIMB Ltd., Ferguson Building, Craibstone Estate, Bucksburn, Aberdeen, AB21 9YA, OK), which is an acceptable depository recognized under the Budapest Treaty, and assigned accession numbers 41294, 41295, 41296, 41297, 41298, 41299, 41300, 41301, 41302, 41303, 41304, 41305, 41306, 41307, 41308, 41309, 41310, 41311, 41312, 41313, 41314, 41315, 41316, 41317, 41318, 41319, 41320, 41321, 41322 or 41323. Deposited seeds will be irrevocably and without restriction or condition released to the public during the term of any patent issued from this application. The M2 population of spinach is a batch of seeds that may each contain one or more mutations, thus forming a pool of mutations. Plants having the reduced susceptibility of the invention can be selected therefrom by screening the plant population as described throughout the specification, including by inoculating M1 plants of the present invention, or progeny thereof, with a pathogen, and selecting plants that show a reduction or absence of sporulation of the pathogen as plants having a reduced susceptibility phenotype.

TABLE 5

Results of downy mildew screen on 32 M3 lines inoculated with race Pfs: 7.

| Nr. | Seed Nr. | Pfs: 7 |
|---|---|---|
| 1 | 05.88528 | Seg |
| 2 | 05.88529 | S |
| 3 | 05.88530 | S |
| 4 | 05.88531 | S |
| 5 | 05.88532 | S |
| 6 | 05.88533 | S |
| 7 | 05.88535 | S |
| 8 | 05.88536 | S |
| 9 | 05.88537 | S |
| 10 | 05.88539 | S |
| 11 | 05.88540 | S |
| 12 | 05.88541 | S |
| 13 | 05.88542 | S |
| 14 | 05.88543 | S |
| 15 | 05.88544 | S |
| 16 | 05.88545 | S |
| 17 | 05.88546 | S |
| 18 | 05.88547 | S |
| 19 | 05.88548 | S |
| 20 | 05.88549 | S |
| 21 | 05.88550 | — |
| 22 | 05.88551 | S |
| 23 | 05.88552 | S |
| 24 | 05.88553 | S |
| 25 | 05.88554 | S |
| 26 | 05.88555 | S |
| 27 | 05.88556 | Seg |
| 28 | 05.88557 | S |
| 29 | 05.88558 | S |
| 30 | 05.88559 | R |
| 31 | 05.88560 | Seg |
| 32 | 05.88561 | S |

S = Susceptible,
Seg = Segregating,
R = resistant

TABLE 6

Deposit information

| mutant no. | RZ deposit no. | seed colour | species | NCIMB number |
|---|---|---|---|---|
| 1 | 05D855B01 | black | *Lactuca sativa* L. | 41294 |
| 2 | 05D855B02 | black | *Lactuca sativa* L. | 41295 |
| 3 | 05D855B03 | black | *Lactuca sativa* L. | 41296 |
| 4 | 05D855B04 | white | *Lactuca sativa* L. | 41297 |
| 5 | 05D855B05 | white | *Lactuca sativa* L. | 41298 |
| 6 | 05D855B06 | white | *Lactuca sativa* L. | 41299 |

TABLE 6-continued

Deposit information

| mutant no. | RZ deposit no. | seed colour | species | NCIMB number |
|---|---|---|---|---|
| 7 | 05D855B07 | white | *Lactuca sativa* L. | 41300 |
| 8 | 05D855B08 | white | *Lactuca sativa* L. | 41301 |
| 9 | 05D855B09 | white | *Lactuca sativa* L. | 41302 |
| 10 | 05D855B10 | white | *Lactuca sativa* L. | 41303 |
| 11 | 05D855B11 | white | *Lactuca sativa* L. | 41304 |
| 12 | 05D855B12 | white | *Lactuca sativa* L. | 41305 |
| 15 | 05D855B15 | white | *Lactuca sativa* L. | 41306 |
| 16 | 05D855B16 | white | *Lactuca sativa* L. | 41307 |
| 17 | 05D855B17 | white | *Lactuca sativa* L. | 41308 |
| 18 | 05D855B18 | white | *Lactuca sativa* L. | 41309 |
| 19 | 05D855B19 | white | *Lactuca sativa* L. | 41310 |
| 20 | 05D855B20 | white | *Lactuca sativa* L. | 41311 |
| 22 | 05D855B22 | white | *Lactuca sativa* L. | 41312 |
| 24 | 05D855B24 | white | *Lactuca sativa* L. | 41313 |
| 25 | 05D855B25 | white | *Lactuca sativa* L. | 41314 |
| 26 | 05D855B26 | white | *Lactuca sativa* L. | 41315 |
| 27 | 05D855B27 | white | *Lactuca sativa* L. | 41316 |
| 28 | 05D855B28 | black | *Lactuca sativa* L. | 41317 |
| 42 | 05D855B42 | white | *Lactuca sativa* L. | 41318 |
| 44 | 05D855B44 | white | *Lactuca sativa* L. | 41319 |
| 45 | 05D855B45 | white | *Lactuca sativa* L. | 41320 |
| 47 | 05D855B47 | white | *Lactuca sativa* L. | 41321 |
| 48 | 05D855B48 | white | *Lactuca sativa* L. | 41322 |
| 49 | 05D855B49 | white | *Lactuca sativa* L. | 41323 |
| — | 03.67551 | — | *Spinacia oleracea* L. | 41324 |

The invention claimed is:

1. A lettuce plant showing a reduced susceptibility towards infection with an oomycete, wherein the plant has genetic information in its genome which is responsible for the reduced susceptibility for oomycetes as in a lettuce plant, representative seed of which was deposited under NCIMB accession number 41294, 41295, 41296, 41297, 41298, 41299, 41300, 41301, 41302, 41303, 41304, 41305, 41306, 41307, 41308, 41309, 41310, 41311, 41312, 41313, 41314, 41315, 41316, 41317, 41318, 41319, 41320, 41321, 41322 or 41323.

2. A progeny of a the plant of claim 1 having all characteristics including reduced susceptibility towards infection with an oomycete as in a lettuce plant, representative seed of which was deposited under NCIMB accession number 41294, 41295, 41296, 41297, 41298, 41299, 41300, 41301, 41302, 41303, 41304, 41305, 41306, 41307, 41308, 41309, 41310, 41311, 41312, 41313, 41314, 41315, 41316, 41317, 41318, 41319, 41320, 41321, 41322 or 41323.

3. A seed of a lettuce plant of showing a reducedsusceptibility towards infection with an oomycete, a representative sample of which seed was deposited under NCIMB accession number 41294, 41295, 41296, 41297, 41298, 41299, 41300, 41301, 41302, 41303, 41304, 41305, 41306, 41307, 41308, 41309, 41310, 41311, 41312, 41313, 41314, 41315, 41316, 41317, 41318, 41319, 41320, 41321, 41322 or 41323.

4. Pollen of the plant of claim 1.

5. A cell of the plant of claim 1.

6. A tissue of the plant of claim 1.

7. A method of producing a lettuce plant, or part thereof, having reduced susceptibility towards infection with an oomycete, comprising producing progeny from a plant, or part thereof, having reduced susceptibility towards infection with the oomycete, representative seed of which having been deposited under NCIMB accession number 41294, 41295, 41296, 41297, 41298, 41299, 41300, 41301, 41302, 41303, 41304, 41305, 41306, 41307, 41308, 41309, 41310, 41311, 41312, 41313, 41314, 41315, 41316, 41317, 41318, 41319, 41320, 41321, 41322 or 41323.

8. A plant produced from the method of claim 7, having all characteristics including reduced susceptibility towards infection with an oomycete as in a lettuce plant, representative seed of which was deposited under NCIMB accession number 41294, 41295, 41296, 41297, 41298, 41299, 41300, 41301, 41302, 41303, 41304, 41305, 41306, 41307, 41308, 41309, 41310, 41311, 41312, 41313, 41314, 41315, 41316, 41317, 41318, 41319, 41320, 41321, 41322 or 41323.

9. A lettuce plant having all characteristics of a lettuce plant grown from seed deposited under NCIMB accession number 41294, 41295, 41296, 41297, 41298, 41299, 41300, 41301, 41302, 41303, 41304, 41305, 41306, 41307, 41308, 41309, 41310, 41311, 41323. 41312, 41313, 41314, 41315, 41316, 41317, 41318, 41319, 41320, 41321, 41322 or 41323.

* * * * *